US00PP28498P2

(12) United States Plant Patent
Horvath

(10) Patent No.: US PP28,498 P2
(45) Date of Patent: Oct. 3, 2017

(54) ***RUDBECKIA* PLANT NAMED 'AMERICAN GOLD RUSH'**

(50) Latin Name: ***Rudbeckia* hybrid**
Varietal Denomination: American Gold Rush

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 59 days.

(21) Appl. No.: 14/756,733

(22) Filed: Oct. 6, 2015

(51) Int. Cl.
*A01H 5/02* (2006.01)

(52) U.S. Cl.
USPC ..... Plt./474

(58) Field of Classification Search
USPC ..... Plt./474
See application file for complete search history.

*Primary Examiner* — June Hwu

(57) ABSTRACT

A new and distinct variety of *Rudbeckia* plant as illustrated and described, characterized by the combination smaller hairy foliage and shorter height, compared to the seed parent.

1 Drawing Sheet

Figure 1:
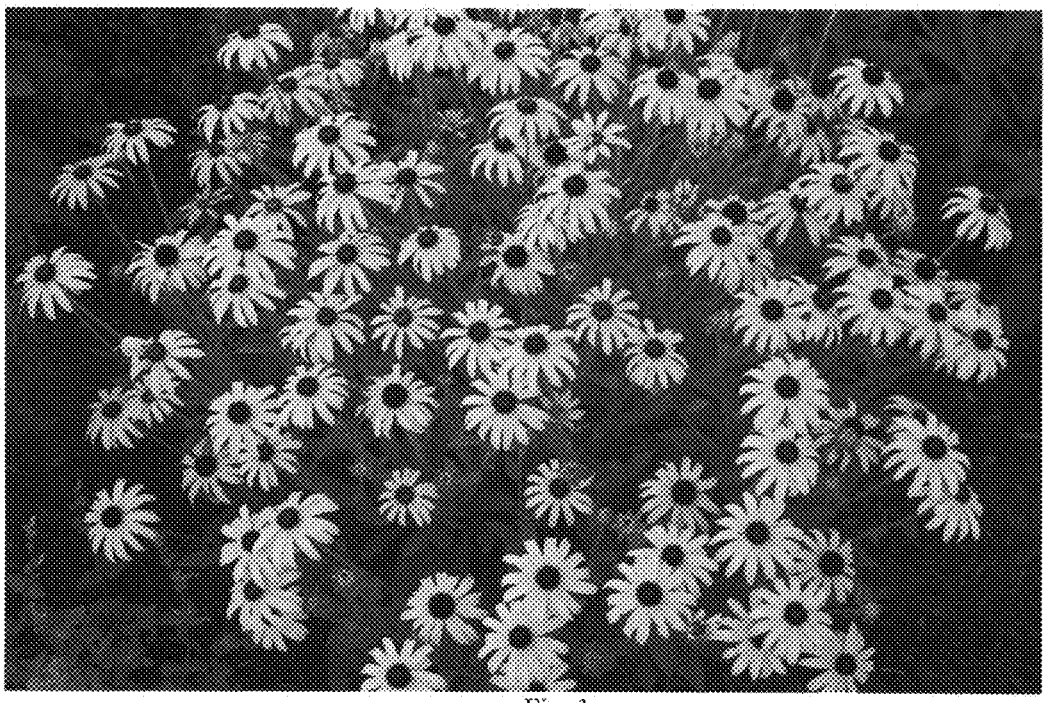

Latin name: *Rudbeckia* hybrid.
Cultivar name: 'American Gold Rush'.

BACKGROUND OF THE INVENTION

The present invention relates to a new and distinct hybrid of *Rudbeckia* plant named 'American Gold Rush' characterized by the combination smaller hairy foliage, shorter height, compared to the seed parent. The new *Rudbeckia* was raised as a seedling from open pollinated seed sown from the seed parent *Rudbeckia fulgida* var. *deamii*, not patented, in Hebron, Ill. in 2011. The selection of the new plant was due to its' smaller hairy foliage and shorter height compared to the seed parent. Initial asexual reproduction has taken place at a nursery in Hebron, Ill. since 2012 by means of division, and stem cuttings. The new *Rudbeckia* has shown to be stable and identical in reproduction to the parent after rooting over 1400 plants from 2012 to 2014.

SUMMARY OF THE INVENTION

The new *Rudbeckia* plant named 'American Gold Rush' characterized by the combination of smaller hairy foliage and shorter height, compared to the seed parent. For purpose of comparison the new plant will be referred to as 'American Gold Rush'.

SUMMARY OF TIM INVENTION

The new *Rudbeckia* plant named 'American Gold Rush' characterized by the combination smaller hairy foliage and shorter height, compared to the seed parent have been observed to be unique and stable.

Plants of the new *Rudbeckia* can be compared to plants of *Rudbeckia fulgida* var. *deamii* the seed parent, not patented.

1. The new *Rudbeckia* plant has a mature size measuring 36 cm high and 39 cm wide while *Rudbeckia fulgida* var. *deamii* measures 120 cm high and over 60 cm wide.
2. The new *Rudbeckia* plant has a naturally mound shaped habit while *Rudbeckia fulgida* var. *deamii* has an upright open habit.

3. The new *Rudbeckia* plant has smaller foliage approximately 25 cm long and 5 cm wide while *Rudbeckia fulgida* var. *deamii* has foliage that reaches approximately 35 cm long and 10 cm wide.

Plants of the new *Rudbeckia* can also be compared to the *Rudbeckia fulgida* 'Early Bird Gold', patented, U.S. Plant Pat. No. 20,286. The new plant has longer foliage, 25 cm in length and soft pubescent foliage while *Rudbeckia fulgida* 'Early Bird Gold' has foliage 13-15 cm in length and rough pubescent foliage.

DESCRIPTION OF PHOTOGRAPHS

Figure 2:
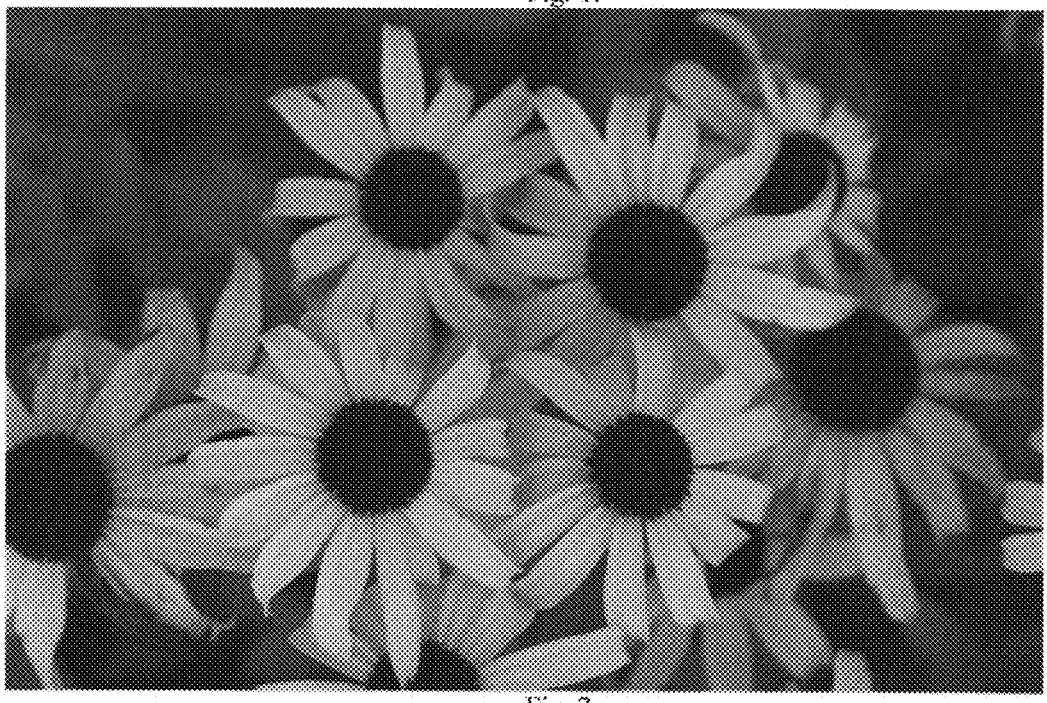

FIG. 1. A blooming 2 year old plant in July.
FIG. 2. A close up of the flower.

DETAILED BOTANICAL DESCRIPTION

In the following description, color references are made to The Royal Horticultural Society Colour Chart 2001 edition. Plants used for the description were grown for two seasons at a nursery in Hebron, Ill. Measurements and numerical values represent averages of typical plants.

Botanical classification: *Rudbeckia* cultivar American Gold Rush.

Parentage: Male or pollen parent an unknown *Rudbeckia*, female or seed parent *Rudbeckia fulgida* var. *deamii.*

Propagation: Vegetative division and stem cutting propagation.

Root description: Fibrous, medium thickness, brown in color.

Root habit: Moderate branching, moderate density.

Plant description: Herbaceous perennial. Overall habit of the new *Rudbeckia* is a mound shaped clump, with branching stems topped by gold inflorescences starting in mid June.

*Plant height.*—36 cm.

*Plant width.*—39 cm.

*Primary stem diameter.*—6-8 mm.

*Primary and secondary stem description.*—Branching, with 20 or more leaves. Leaves get smaller as they go up the stem. Strength — strong.

*Primary and lateral stem texture.*—Pubescent with, hairs up to 2 mm long.

*Secondary stem description.*—Average 10 lateral stems per primary stem.
*Secondary stem length.*—22 cm.
*Secondary stem diameter.*—3 mm.
*Secondary stem internodes.*—3 cm.
*Stem color.*—N 144 A.

Foliage:
*Type.*—Herbaceous.
*Leaf arrangement.*—Alternate, simple, sessile.
*Length.*—25 cm.
*Width.*—5 cm.
*Shape.*—Lanceolate.
*Apex.*—Acute.
*Base.*—Attenuate.
*Margin.*—Dentate.
*Texture.*—Pubescent, soft.
*Venation.*—Pinnate. Venation Color — 145 C.
*Adaxial leaf description.*—Color is 146 A including developing, fully expanded.
*Abaxial leaf description.*—Color is 146 B including developing, fully expanded.

Bud:
*Bud Shape.*—Oblate.
*Bud length.*—12 mm.
*Bud diameter.*—12 mm.
*Bud color.*—145 C.

Inflorescence:
*Inflorescence type.*—Single, composite on branched flowering stems.
*Position.*—Borne on both terminal and axillary peduncles above the foliage.
*Number of inflorescences per plant.*—Approximately 150.
*Arrangement.*—Disc and ray florets.
*Mature center disc.*—20 mm wide and 13-15 mm height.
*Number of disc florets.*—300, number of ray florets 13-14.
*Immature disc floret color.*—152 C.
*Mature Disc floret color.*—Dark brown but close to 202 A.
*Disc floret diameter.*—2-3 mm at apex, 1-2 mm at base.
*Disc floret shape.*—Rotate.
*Disc floret length.*—4 mm.
*Disc floret width.*—2 mm.
*Disc floret apex.*—Acute.
*Disc floret margin.*—Entire.
*Disc floret count.*—13-14.
*Ray floret size.*—25-26 mm length and 8 mm width.
*Ray floret color upon opening and in full bloom.*—Adaxial 17 A and Abaxial 17 C.
*Ray floret aspect.*—Initially incurved, then upright, then perpendicular to the peduncle.
*Ray floret shape.*—Lanceolate.
*Ray floret apex.*—Emarginate.
*Ray floret base.*—Obtuse.
*Ray floret margin.*—Entire.
*Ray floret count.*—Approximately 12-15 per inflorescence
*Ray floret texture.*—Both the upper and lower surfaces axe smooth, glabrous.
*Overall inflorescence size.*—6 cm or more across in diameter with ray florets, 1 cm in height. Receptacle height — 9 mm, diameter 3 cm across.
*Bloom period and duration.*—Mid June through mid-September. 4-6 weeks on the plant.
*Blooming habit.*—Domed, upright on 45-60 cm terminal flowering stems.

Phyllaries:
*Number of phyllaries per inflorescence.*—15 average.
*Length.*—10 mm.
*Width.*—3 mm.
*Shape.*—Lanceolate.
*Apex.*—Mucronate.
*Base.*—Fused.
*Margin.*—Entire.
*Texture.*—Both upper and lower surface scattered pubescence.
*Color.*—Adaxial 146 C and Abaxial 146 A.

Peduncles:
*Length of both terminal and axillary peduncles.*—10 cm.
*Diameter.*—2 mm.
*Angle.*—Erect to about 55 degrees from vertical.
*Strength.*—Strong, Texture — pubescent, Color — 146 C.

Reproductive organs:
*Androecium.*—Quantity per disc floret, 5.
*Filament length.*—3-4 mm.
*Filament color.*—145 C.
*Anther shape.*—Oblong.
*Anther length.*—1 mm.
*Anther color.*—17 C.
*Pollen amount.*—None observed.
*Gynoecium present on ray and disc florets.*—
*Pistils.*—One, length 3 mm.
*Stigma shape.*—Two parted, Stigma color — 202 A.
*Style length.*—4 mm, Style color — 202 A.
*Scent.*—No scent noticed.

Seed and fruit: None observed.

Disease resistance: Resistance to diseases common to *Rudbeckia* has not been observed on plants grown under nursery conditions.

Hardiness: Plants of the new *Rudbeckia* have been observed to be hardy to USDA Zone 5.

I claim:

1. A new and distinct variety of *Rudbeckia* plant as illustrated and described, characterized by the combination smaller hairy foliage and shorter height, compared to the seed parent.

* * * * *